(12) United States Patent
Chuang et al.

(10) Patent No.: US 10,214,719 B2
(45) Date of Patent: Feb. 26, 2019

(54) **METHOD OF CULTURING *ANTRODIA CINNAMOMEA* WITH HIGH TRITERPENOIDS**

(71) Applicant: Ultra-Microrigin Biomedical Technology Co., Ltd., Zhubei (TW)

(72) Inventors: Ming-Hsi Chuang, Zhubei (TW); Chu-Ting Liu, Zhubei (TW); I-Lung Yu, Zhubei (TW); Lin-Hsiang Chuang, Zhubei (TW)

(73) Assignee: Ultra-Microrigin Biomedical Technology Co., Ltd., Zhubei (TW)

( * ) Notice: Subject to any disclaimer, the term of this patent is extended or adjusted under 35 U.S.C. 154(b) by 0 days.

(21) Appl. No.: 15/675,985

(22) Filed: Aug. 14, 2017

(65) Prior Publication Data

US 2017/0342369 A1 Nov. 30, 2017

Related U.S. Application Data

(63) Continuation of application No. 15/070,132, filed on Mar. 15, 2016, now abandoned.

(30) Foreign Application Priority Data

Dec. 2, 2015 (TW) .............................. 104140435 A

(51) Int. Cl.
| | |
|---|---|
| A61L 2/02 | (2006.01) |
| C12P 5/00 | (2006.01) |
| A01G 18/00 | (2018.01) |
| C12N 13/00 | (2006.01) |
| C12N 1/14 | (2006.01) |

(52) U.S. Cl.
CPC .................. *C12N 1/14* (2013.01); *A61L 2/02* (2013.01); *C12N 13/00* (2013.01); *C12P 5/007* (2013.01); *A01G 18/00* (2018.02)

(58) Field of Classification Search
None
See application file for complete search history.

*Primary Examiner* — Kade Ariani
(74) *Attorney, Agent, or Firm* — Jackson IPG PLLC; Demian K. Jackson

(57) ABSTRACT

A method of culturing *Antrodia cinnamomea* with high Triterpenoids includes mixing a malt extract, glucose, peptone, agar, and a mushroom's extract with distilled water to obtain a culture medium; providing the culture medium to a high-pressure sterilization machine for sterilization to obtain a sterilized culture medium; providing the sterilized culture medium to an incubator in a disinfection environment to obtain a solidified culture medium after a predetermined time; transplanting *Antrodia cinnamomeas* strains to the solidified culture medium at separated positions; and exposing the solidified culture medium under a beam.

3 Claims, 2 Drawing Sheets

METHOD OF CULTURING *ANTRODIA CINNAMOMEA* WITH HIGH TRITERPENOIDS

BACKGROUND OF THE INVENTION

1. Technical Field

The present invention relates generally to a method of culturing *Antrodia cinnamomea*, and more particularly to a method of culturing *Antrodia cinnamomea* with high Triterpenoids.

2. Description of Related Art

*Antrodia cinnamomea* is a fungal parasite grown in inner cavities of the endemic species *Cinnamomum kanehirae*. *Antrodia cinnamomea* is widely used in Chinese society to be a medicine for food/medicine poisoning, diarrhea, abdominal pain, hypertension, and cancer. *Antrodia cinnamomea* is high-economically valued, and can be made into various medicines and healthy foods. *Antrodia cinnamomea* contains high Triterpenoids in its fruiting bodies, and Triterpenoids is effective in deactivating tumor cells and killing cancer cells without affecting the normal cells.

There are some traditional methods of culturing fruiting bodies of *Antrodia cinnamomea*. For example, TWI422680 and CN102746054 disclose a conventional culture medium for culturing microorganisms, in which specified Chinese medicine extracts are received. The culture medium is put in a sterile room with a controlled environment for 135 days to obtain a solidified culture medium for culturing *Antrodia cinnamomea*. CN202455895 discloses a sterile box to culture *Antrodia cinnamomea*, the environment in the sterile box is controlled as well, and *Antrodia cinnamomea* is exposed under 300 nm-800 nm light to increase the culturing efficiency of *Antrodia cinnamomea* in lindens, and to increase the active components thereof. In the prior arts as mentioned above, they need the expensive equipment to control the environment of the sterile room and a lot of expensive Chinese medicine extracts (about 16.7%-40%), and furthermore, they have to take at least 5 months (it would take 24 months when culturing in lindens) to culture *Antrodia cinnamomea*. The cost is expensive, and need plenty of energy.

Typically, there are four major categories of culturing *Antrodia cinnamomea* in the present market, and they are: 1) culturing *Antrodia cinnamomea* in *Cinnamomum kanehirae* or lindens; 2) culturing *Antrodia cinnamomea* by solidified culture medium; 3) culturing mycelium of *Antrodia cinnamomea* by liquid fermentation; and 4) culturing *Antrodia cinnamomea* in plastic bags. The first category is limited by rarer and rarer *Cinnamomum kanehirae* and lindens could be obtained. The fruiting bodies of *Antrodia cinnamomea* have Triterpenoids no matter it was cultured by the first or the second categories. No Triterpenoids in *Antrodia cinnamomea* when it was cultured by the third category, but culturing time is short which is beneficial to mass production. However, there is a large variation in the mycelium and fruiting bodies. Using the fourth category, it could have a similar aspect as wild *Antrodia cinnamomea*, but also have problems of high wood fibers and low Triterpenoids.

In conclusion, the fruiting bodies of *Antrodia cinnamomea* cultured by the first and the second categories contain Triterpenoids, which means they are better than *Antrodia cinnamomea* cultured by the third and fourth categories. However, the second category has the problems of high cost and needing long time (about two years) for culturing. It is bad for mass production and promotion.

BRIEF SUMMARY OF THE INVENTION

In view of the above, the primary objective of the present invention is to provide a method of culturing *Antrodia cinnamomea* with high Triterpenoids, which cultures *Antrodia cinnamomea* without lindens and in a normal environment. The culturing time is about one month, and *Antrodia cinnamomea* contains high Triterpenoids. Furthermore, the present invention is cheap, recyclable, save, and high economic.

The present invention provides a culturing *Antrodia cinnamomea* with high Triterpenoids, including well mixing a malt extract, glucose, peptone, agar, and a mushroom's extract with distilled water to obtain a culture medium; providing the culture medium to a high-pressure sterilization machine for sterilization in a predetermined pressure, a predetermined pressure, and a predetermined time to obtain a sterilized culture medium; providing the sterilized culture medium to an incubator in a disinfection environment to cool the sterilized culture medium and to obtain a solidified culture medium after a predetermined time; transplanting *Antrodia cinnamomeas* strains to the solidified culture medium at separated positions; and exposing the solidified culture medium under a beam with a predetermined wavelength and a predetermined illuminance for a predetermined time to obtain *Antrodia cinnamomeas* with high Triterpenoids.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

The detailed description and technical contents of the present invention will be explained with reference to the accompanying drawings. However, the drawings are for illustration only and cannot be used to limit the present invention.

Figure 1:
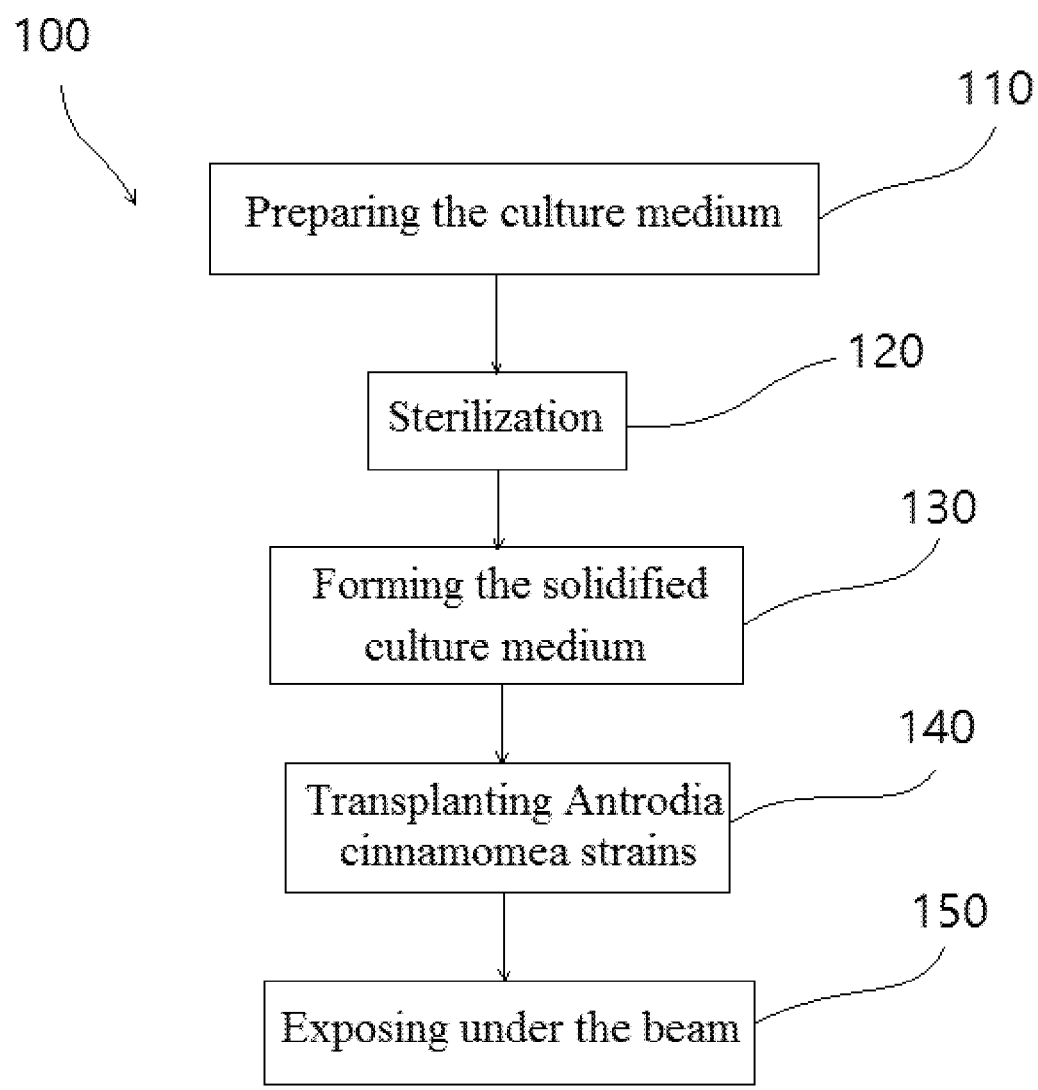
FIG. 1 is a flow chart of a preferred embodiment of the present invention.

As shown in FIG. 1, a method 100 of culturing *Antrodia cinnamomea* with high Triterpenoids of the preferred embodiment of the present invention includes the following steps:

First step 110: preparing a culture medium. The culture medium includes 1%-2% w/v malt extract, 1%-2% w/v glucose, 0.1%-0.2% w/v peptone, 1%-2% w/v agar, and 0.1%-0.2% w/v mushroom extract (such as the extract of *Flammulina velutipes*, *Auricularia auricula-judae*, *Tremella fuciformis*, and/or *Lentinus edodes*). These components are put in a glass container, and well mixed with distilled water.

Second step 120: sending the culture medium to a high-pressure sterilization machine to sterilize under 1 kg/cm² and 120° C-121° C. for 25-30 minutes. In the present embodiment, the high-pressure sterilization machine is a high-pressure sterilization caldron.

Third step 130: forming a solidified culture medium. The sterilized culture medium is put in an incubator in a disinfection environment (such as a disinfection working table). A diameter of the incubator is 90 mm, a height is 10 mm. A deep of the sterilized culture medium in the incubator is 1 mm (about 6 cc). The sterilized culture medium in the incubator is cooled for a predetermined time to form the solidified culture medium.

Fourth step 140: transplanting *Antrodia cinnamomea* strains to the solidified culture medium at separated positions. A planting area of each strain is about 1 mm×1 mm. The strains are planted at a top, a bottom, a right, a left, and a center of the solidified culture medium, and an interval between the neighboring strains is about 20 mm.

Fifth step 150: exposing the solidified culture medium under a specific beam. The solidified culture medium is kept in room temperature (25° C.-30° C.), and exposed under a beam of 620-625 nm (red light) and 400-600 Lux for 30 days to obtain *Antrodia cinnamomeas* with high Triterpenoids.

The method of the present invention includes preparing the culture medium, sterilization, forming the solidified culture medium, transplanting the strains, and exposed under the specific beam that could obtain *Antrodia cinnamomeas* with high Triterpenoids in a month.

Figure 2:
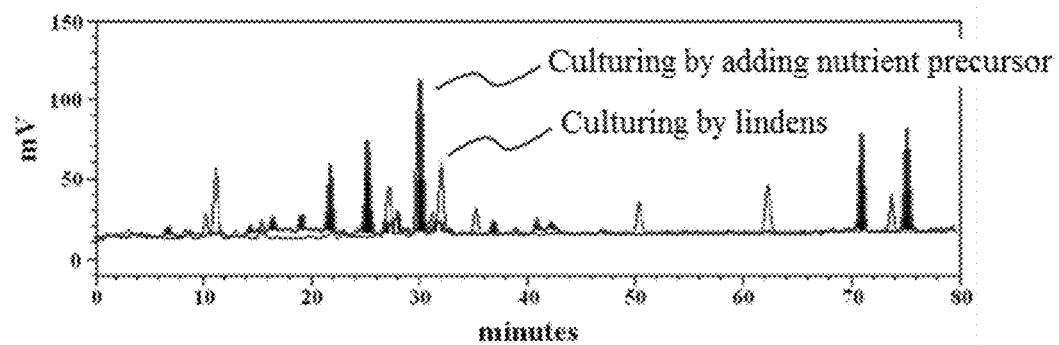
FIG. 2 is a HPLC diagram, showing Triterpenoids in the fruiting bodies of the *Antrodia cinnamomeas* cultured by the method of the present invention with the culture medium of mushroom's nutrient precursor and by lindens.

We compare fruiting bodies of the *Antrodia cinnamomeas* obtained by the method of the present invention with fruiting bodies of the *Antrodia cinnamomeas* obtained by culturing in lindens, and the results are listed hereafter:

As shown in FIG. 2, Triterpenoids in the fruiting bodies of the *Antrodia cinnamomeas* of the present invention and in the fruiting bodies of the *Antrodia cinnamomeas* of lindens are the same, which means that the present invention provides the same fruiting bodies of *Antrodia cinnamomeas* as the conventional *Antrodia cinnamomeas* of lindens.

The concentrated solution of *Flammulina velutipes, Auricularia auricula-judae, Tremella fuciformis*, and/or *Lentinus edodes* is helpful to directly forming Triterpenoids in the fruiting bodies of *Antrodia cinnamomeas*. Therefore, the nutrient precursor of the present invention is helpful to fast growing of Triterpenoids in the fruiting bodies of *Antrodia cinnamomeas*. The culture medium of the conventional nutrient precursor provides the strains growing a solidified environment, which is similar to a natural growing condition. The present invention also provides high-temperature sterilization step to ensure the quality thereof.

The conventional culturing method by lindens uses is transplanting *Antrodia cinnamomea* trains to a dead *Cinnamomum kanehirae*. The trains grow in the *Cinnamomum kanehirae* to obtain the fruiting bodies of *Antrodia cinnamomea*. The growing time is about two years that is bad for mass production and promotion, which shows that the present invention has high economic value.

Figure 3:
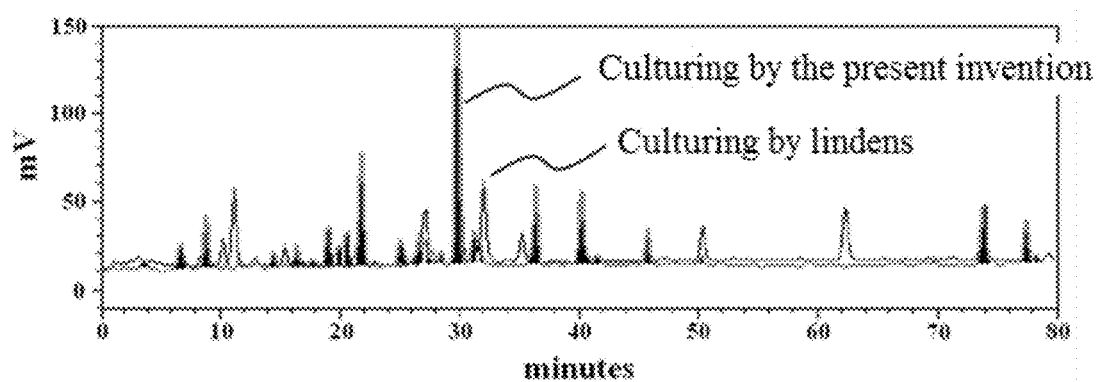
FIG. 3 is HPLC diagram, showing Triterpenoids in the fruiting bodies of the *Antrodia cinnamomeas* cultured by the method of the present invention and by lindens.

In addition, in the induction test of the fruiting bodies, exposure under the red light and stimulation of the nutrient precursor are helpful to forming high Triterpenoids in the fruiting bodies of *Antrodia cinnamomeas*. The function of forming Triterpenoids in the fruiting bodies is up to nutrient and environment. For example, adding nutrient precursor and light stimulation are helpful to forming Triterpenoids in the fruiting bodies of *Antrodia cinnamomeas*. FIG. 3 shows that the Triterpenoids in the fruiting bodies of *Antrodia cinnamomeas* of the present invention is higher than that of culturing in lindens.

In conclusion, the advantages of the present invention include:

1. The fruiting bodies of *Antrodia cinnamomeas* are cultured in the incubator, which shortens the culturing time to four weeks, and increases the culturing success (about 95%-98%). It is helpful to mass production and promotion.

2. The culturing medium of nutrient precursor of the present invention increases the culturing efficiency of *Antrodia cinnamomea*, and stabilize the production of Triterpenoids in the fruiting bodies of *Antrodia cinnamomea*.

3. The light stimulation of the present invention is helpful to growth of the fruiting bodies of *Antrodia cinnamomea* as well as the increasing of Triterpenoids in the fruiting bodies of *Antrodia cinnamomea*.

It must be pointed out that the embodiments described above are only some preferred embodiments of the present invention. All equivalent structures which employ the concepts disclosed in this specification and the appended claims should fall within the scope of the present invention.

What is claimed is:

1. A method of culturing *Antrodia cinnamomea* with high triterpenoids, comprising the steps of:
    preparing a culture medium (nutrient precursor): mixing a malt extract, glucose, peptone, agar, and a mushroom's extract with distilled water to obtain a culture medium, the culture medium includes 1%-2% w/v of the malt extract, 1%-2% w/v of the glucose, 0.1%-0.2% w/v of the peptone, 1%-2% w/v of the agar, and 0.1%-0.2% w/v of a concentrated solution of mushroom extract, wherein, the mushroom extract is the concentrated solution of *Flammulina velutipes, Auricularia auricular-judae, Tremella fuciformis*, or *Lentinus edodes*;
    sterilization: placing the culture medium in a high-pressure sterilization machine for sterilization in a pressure of 1 kg/cm², and 120° C-121° C. for 25-30 minutes to obtain a sterilized culture medium;
    forming a solidified culture medium by: placing the sterilized culture medium in an incubator in a disinfection environment to cool the sterilized culture medium and to obtain a solidified culture medium after a predetermined time;
    transplanting *Antrodia cinnamomea* strains : transplanting *Antrodia cinnamomea* strains, wherein are transplanted at a top, a bottom, a right, a left, and a center of the solidified culture medium, and an separated interval between the neighboring strains; and
    exposing under a specific beam, wherein: exposing the solidified culture medium to red light with a wavelength of 620-625 nm and an illuminance of 400-600 Lux for thirty days in 25° C-30° C;
    thereby, exposure under the red light and stimulation of the nutrient precursor increases the production of triterpenoids in the fruiting bodies of *Antrodia cinnamomeas*.

2. The method as defined in claim 1, wherein the sterilized culture medium is put in an incubator with a diameter of 90 mm and a height of 10 mm, a depth of the sterilized culture medium in the incubator is 1 mm.

3. The method as defined in claim 1, wherein the separated interval between the neighboring strains is 20 mm.

* * * * *